(12) United States Patent
Barry et al.

(10) Patent No.: US 7,122,800 B2
(45) Date of Patent: Oct. 17, 2006

(54) OPTICAL DENSITY SENSOR

(75) Inventors: Raymond Jay Barry, Lexington, KY (US); Gary Scott Overall, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 286 days.

(21) Appl. No.: 10/810,732

(22) Filed: Mar. 26, 2004

(65) Prior Publication Data

US 2005/0211902 A1  Sep. 29, 2005

(51) Int. Cl.
*G01J 5/02* (2006.01)
*G03G 15/00* (2006.01)

(52) U.S. Cl. .................. 250/341.1; 399/15; 399/64

(58) Field of Classification Search ........... 250/340, 250/341.1, 342, 228, 559.07; 356/399; 399/15, 399/64
See application file for complete search history.

(56) References Cited

U.S. PATENT DOCUMENTS

| | | | |
|---|---|---|---|
| 1,834,905 A | 12/1931 | Sheldon | |
| 1,960,169 A | 5/1934 | Schoenberg | |
| 1,964,365 A | 6/1934 | Razek et al. | |
| 1,979,952 A | 11/1934 | Benford | |
| 2,107,836 A | 2/1938 | Pineo | |
| 2,263,938 A | 11/1941 | West | |
| 2,347,067 A | 4/1944 | Shurcliff | |
| 2,383,346 A | 8/1945 | Shurcliff | |
| 2,707,900 A | 5/1955 | Maresh et al. | |
| 2,992,588 A | 7/1961 | Henderson | |
| 3,327,583 A | 6/1967 | Vanderschmidt et al. | |
| 3,874,799 A | 4/1975 | Isaacs et al. | |
| 3,935,436 A | 1/1976 | Holschlag et al. | |
| 4,232,971 A | 11/1980 | Suga | |
| 4,278,887 A | 7/1981 | Lipshutz et al. | |
| 4,980,727 A * | 12/1990 | Stelter | 399/64 |
| 5,204,538 A * | 4/1993 | Genovese | 250/559.07 |
| 5,253,018 A * | 10/1993 | Takeuchi et al. | 399/49 |
| 5,548,120 A * | 8/1996 | Parker et al. | 250/341.7 |
| 5,625,857 A * | 4/1997 | Shimada et al. | 399/49 |
| 5,650,843 A * | 7/1997 | Moberg et al. | 356/236 |
| 6,004,003 A * | 12/1999 | Dalton et al. | 362/186 |
| 6,225,622 B1 * | 5/2001 | Navarro | 250/252.1 |

* cited by examiner

*Primary Examiner*—David Porta
*Assistant Examiner*—Faye Boosalis
(74) *Attorney, Agent, or Firm*—Coats and Bennett, PLLC

(57) ABSTRACT

An optical density sensor disposed over a target surface in an image formation apparatus comprises an integrating cavity having a diffuse, reflective interior surface and a view port formed therein. An optical source directs light through the view port onto the target surface, without striking any interior surface of the cavity. Light reflected from the target surface is detected by an optical detector disposed within the cavity. The optical source may be disposed in a collimator, which may extend into the interior of the cavity, and may include a lens. A circuit card which may include an optical detector sensing circuit may be disposed proximate the optical detector. A compensating slot formed in the cavity may allow some reflected light to directly impact the optical detector as the gap between the cavity and the target surface increases.

40 Claims, 7 Drawing Sheets

OPTICAL DENSITY SENSOR

BACKGROUND

The present invention relates generally to the field of electrophotography and in particular to an optical density sensor.

Electrophotographic image forming devices optically form a latent image on a photoconductive member, and develop the image by applying toner. The toner is then transferred—either directly or indirectly—to a media sheet where it is deposited and fixed, such as by thermal fusion. In particular, it is known to successively transfer developed color-plane images from one or more photoconductive members to an intermediate transfer belt, and subsequently transfer the developed image to a media sheet for fixation thereon. Examples of an image forming device utilizing an intermediate transfer belt are the Model C750 and C752 printers from Lexmark International, Inc. Alternatively, it is known to direct a single media sheet past one or more photoconductive members, each of which successively transfers a developed color-plane image directly to the media sheet.

A problem common to all electrophotographic image forming devices, regardless of their configuration or operation, is image registration. Image registration refers to the placement of a developed color-plane image, either relative to other color-plane images or relative to the media sheet (i.e., margins, skew and the like). Numerous methodologies are known in the art for measuring and correcting registration errors. Many of these include the steps of transferring developed images comprising test patterns of various forms to a surface and detecting the developed images on the surface, i.e., detecting the presence of toner on the surface. The surface may comprise an intermediate transfer belt, media sheet or the like. In some applications, for registration purposes toner may be deposited directly on a media sheet transport belt, which normally carries the media sheets, without a media sheet being present. Regardless of the surface on which toner is deposited, one way to detect the toner is by the use of optical density sensors.

Optical density sensors are well known in the art. An optical density sensor measures the presence, and preferably the amount (e.g., in gm/cm$^2$), of toner on a surface. This measurement may be performed indirectly, such as by sensing the differing optical properties of the surface and of toner deposited on the surface. One way to sense these properties is to illuminate the surface with a light source—preferably a collimated light source—and sensing and measuring the resulting reflections. Reflections may be generally classified as specular or diffuse. Specular reflection is reflection from a smooth surface, and tends to comprise a sharply defined beam. Diffuse reflection is reflection from a rough surface, in which a collimated beam emerges in all directions. Reflected light sensed and/or measured by an optical density sensor may include components of both specular and diffuse reflections, although one or the other may dominate, depending on the texture and other properties of the surface. The sensed optical properties are translated to toner density through calibration procedures, as well known in the art.

One known form of optical density sensor is called an integrating cavity reflectometer (also known in the art as an integrating sphere reflectometer), a representive schematic diagram of which is depicted in FIG. 15, and indicated generally by the numeral 40. The reflectometer comprises an integrating cavity 42 having a diffuse, highly reflective interior surface 44. A light source, such as a light emitting diode (LED) 46 is disposed in a collimator 48, and emits collimated light through the cavity 42 and out a view port 50, onto a surface 52. The purpose of the collimator 48 is to form a non-divergent beam of light so that all of the light that comes into the cavity 42 from the source 46 will go out the view port 50. Any light from the source 46 that directly hits the interior surface 44 will corrupt the measurement. Light incident on the target surface 52 will be absorbed or reflected (and/or transmitted if the target surface 52 is transparent). If the cavity 42 is in contact with the target surface 52, or very close to it, the reflected light enters the cavity 42, where it is reflected by the interior surface 44 until it is absorbed or strikes an optical detector 54, such as a photodiode, disposed within the cavity 42. Light striking the optical detector 54 generates a voltage and/or current proportional to its intensity, which can be sensed and/or measured. The amount of light striking the optical detector 54 is proportional to the amount reflected from the target surface 52.

The optical density sensor 40 of the type depicted in FIG. 15 is deficient in several respects. The collimator 48 is necessarily long, and difficult to integrate into a compact image forming device. In addition, a large amount of light is lost in the collimator 48, which reduces the signal-to-noise ratio of the detected light, and requires sophisticated electronics and careful calibration to obtain satisfactory results, particularly when measuring black toner, which is very absorptive and reflects relatively little light into the cavity 42. Finally, because the target surface 52 is moving (e.g., an intermediate transfer belt, media sheet or media sheet transport belt), the cavity 42 cannot contact the target surface 52, but rather must be disposed some distance above it. This distance has a strong influence on the detected signal level, since with increasing distance, more reflected light escapes and is not captured by the cavity 42. Any variation in this distance prohibits repeatable measurements; however the distance often varies as a function of age, mechanical mounting tolerances, belt motion, temperature, or even due to inconsistent belt thickness.

SUMMARY

The present invention relates to an optical density sensor for sensing toner on a surface in an image forming device. The reflectometer includes an integrating cavity having a diffuse, reflective inner surface and having a view port formed therein. An optical source is disposed in a collimator and positioned to illuminate the surface through the view port, with the collimator extending into the integrating cavity. An optical detector is disposed within the integrating cavity outside of a direct optical path of the source.

In another aspect, the reflectometer of the present invention includes a circuit card disposed proximate the optical source and the optical detector. The circuit card includes at least one of an optical source drive circuit and an optical detector sensing circuit.

In yet another aspect, the reflectometer of the present invention includes a compensating slot formed in the integrating cavity and positioned to allow light reflected from the surface to directly strike the optical detector when the view port is spaced apart from the surface.

In still another aspect, the reflectometer of the present invention includes a collimator extending into the integrating cavity; a circuit card including at least one of an optical source drive circuit and an optical detector sensing circuit disposed proximate the optical source and the optical detector; and a compensating slot formed in the integrating cavity and positioned to allow light reflected from the surface to directly strike the optical detector when the view port is spaced apart from the surface. The collimator may additionally include a lens.

DETAILED DESCRIPTION

Figure 1:
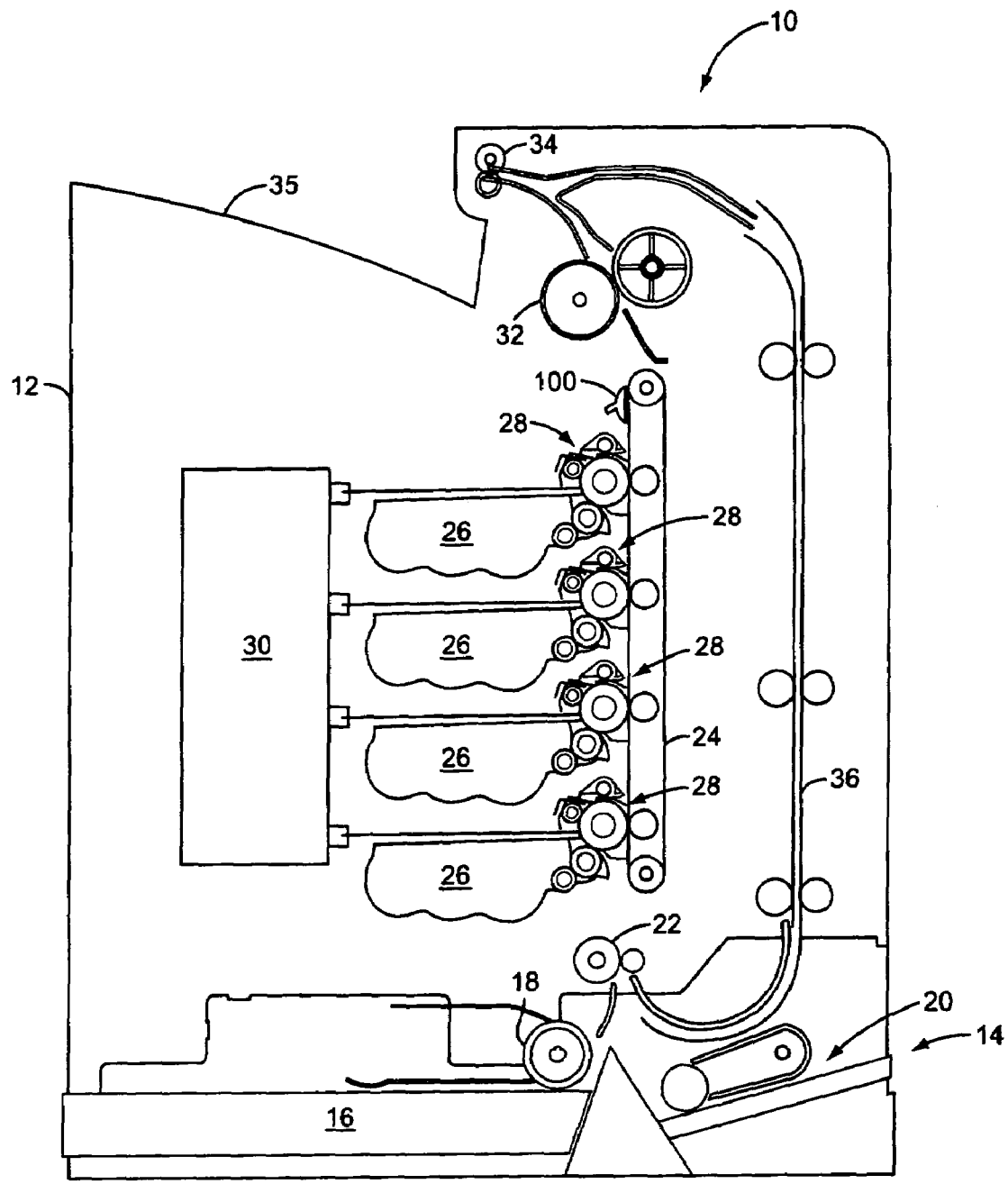
FIG. 1 is a schematic diagram of a representative image forming device having an optical density sensor.

FIG. 1 depicts a representative image forming device, indicated generally by the numeral 10. The image forming device 10 comprises a housing 12 and a media tray 14. The media tray 14 includes a main media sheet stack 16 with a sheet pick mechanism 18, and a multipurpose tray 20 for feeding envelopes, transparencies and the like. The media tray 14 is preferably removable for refilling, and located on a lower section of the device 10.

Within the image forming device body 12, the image forming device 10 includes media registration roller 22, a media sheet transport belt 24, one or more removable developer units 26, a corresponding number of removable photoconductor units 28, an optical density sensor 100, an imaging device 30, a fuser 32, reversible exit rollers 34, and a duplex media sheet path 36, as well as various additional rollers, actuators, sensors, optics, and electronics (not shown) as are conventionally known in the image forming device arts, and which are not further explicated herein.

Each developer unit 26 mates with a corresponding photoconductor unit 28, with the developer unit 26 developing a latent image on the surface of a photoconductive member in the photoconductor unit 28 by supplying toner. Alternatively, the developer and photoconductor units may be integrated into a single cartridge, as well known in the art. In a typical color printer, three or four colors of toner—cyan, yellow, magenta, and optionally black—are applied successively (and not necessarily in that order) to a print media sheet to create a color image. Correspondingly, FIG. 1 depicts four pairs of developer units 26 and photoconductor units 28.

The operation of the image forming device 10 is conventionally known. Upon command from control electronics, a single media sheet is "picked," or selected, from either the primary media stack 16 or the multipurpose tray 20. Alternatively, a media sheet may travel through the duplex path 36 for a two-sided print operation. Regardless of its source, the media sheet is presented at the nip of registration roller 22, which aligns the media sheet and precisely times its passage on to the image forming stations downstream. The media sheet then contacts the transport belt 24, which carries the media sheet successively past the photoconductor units 28. At each photoconductor unit 28, a latent image is formed by the imaging device 30 and optically projected onto a photoconductive member. The latent image is developed by applying toner to the photoconductive member from the corresponding developer unit 26 (or alternatively from a developer roller and toner supply within the cartridge housing the photoconductive member). The toner is subsequently deposited on the media sheet as it is conveyed past the photoconductor unit 28 by the transport belt 24.

The toner is thermally fused to the media sheet by the fuser 32, and the sheet then passes through reversible exit rollers 34, to land facedown in the output stack 35 formed on the exterior of the image forming device body 12. Alternatively, the exit rollers 34 may reverse motion after the trailing edge of the media sheet has passed the entrance to the duplex path 36, directing the media sheet through the duplex path 36 for the printing of another image on the back side thereof.

To facilitate image registration operations, the image-forming apparatus 10 includes one or more optical density sensors 100 (which may alternatively comprise sensors 102, 104, 106, all discussed in greater detail herein), disposed over the media transport belt 24, downstream of the image formation stations 26/28. The optical density sensor 100 (in conjunction with control and signal processing electronics, not shown in FIG. 1) is operative to detect and measure the density of toner deposited on media sheets or directly onto the transport belt 24. A plurality of optical density sensors 100 may be employed, such as for example, positioning two sensors 100 aligned along the scan direction (i.e., perpendicular to the direction of media travel) to detect image skew.

Although shown in FIG. 1 as detecting and measuring toner density on the transport belt 24, the optical density sensor 100 according to the present invention may be advantageously utilized in other image-forming apparatus embodiments, such as detecting toner deposited on an intermediate transfer belt or media sheets. Furthermore, the optical density sensor 100 may be advantageously located in other positions within the image forming device 10. For example, where registration operations are carried out on only the transport belt 24 and not on media sheets, the sensor 100 may be located on the "back" side of the transport belt 24, which may be advantageous in some embodiments, such as where the image forming stations 26/28 leave little room on the "front" side of the transport belt 24.

Figure 2:
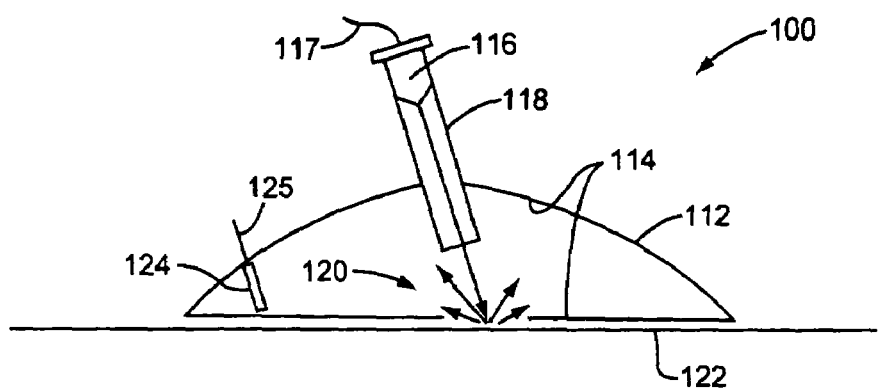
FIG. 2 is schematic diagram of an optical density sensor having a collimator extending into an integrating cavity.

One embodiment of an optical density sensor according to the present invention is depicted in schematic form in FIG. 2, and indicated generally by the numeral 100. The optical density sensor 100 includes an integrating cavity 112 having a diffuse, reflective interior surface 114. An optical source 116, which may for example comprise an LED, is disposed in a collimator 118, and connected by one or more electrical conductors 117 to an optical source drive circuit (not shown). The optical source 116 and collimator 118 are arranged so as to direct collimated light from the optical source 116 through a view port 120 to strike a target surface 122. The light is reflected from the target surface 122, with the majority of the reflected light returning to the integrating cavity 112. The reflected light will reflect off of various interior surfaces 114, until it is absorbed or strikes an optical detector 124, which may comprise a photodiode, connected via one or more electrical conductors 125 to an optical detector sensing circuit (not shown).

According to the present invention, the collimator 118 extends into the integrating cavity 112. This configuration presents several advantages. Bringing the tip of the collimator 118 closer to the target surface 122 reduces the degree of collimation needed because there is less distance for the light to diverge and consequently hit an interior surface 114 of the cavity 112. A lower level of collimation means the collimator 118 can be shorter, bringing the optical source 116 even closer to the target surface 122. The closer proximity of the optical source 116 to the target surface 122 and the reduced losses in the shorter collimator 118 greatly increase the collimator 118 efficiency, as measured by the amount of light hitting the target surface 122. This may allow in a reduction in the drive current for the optical source 116 (such as when the optical source 116 is an LED), and the use of a smaller, lower cost optical detector 124. Furthermore, the improved signal-to-noise ratio allows the use of unshielded conductors 125 to the photodiode, further reducing cost.

The primary liability stemming from the collimator 18 extending into the interior of the cavity 112 is that it may absorb light reflected around inside the cavity, reducing the efficiency of the cavity. This can be minimized by careful placement of the collimator 118 within the cavity 112. In particular, the collimator 118 should be positioned so that it does not block too much of the specular component of the reflection, since the objective is to capture both specular and diffuse components of reflection.

Figure 3:
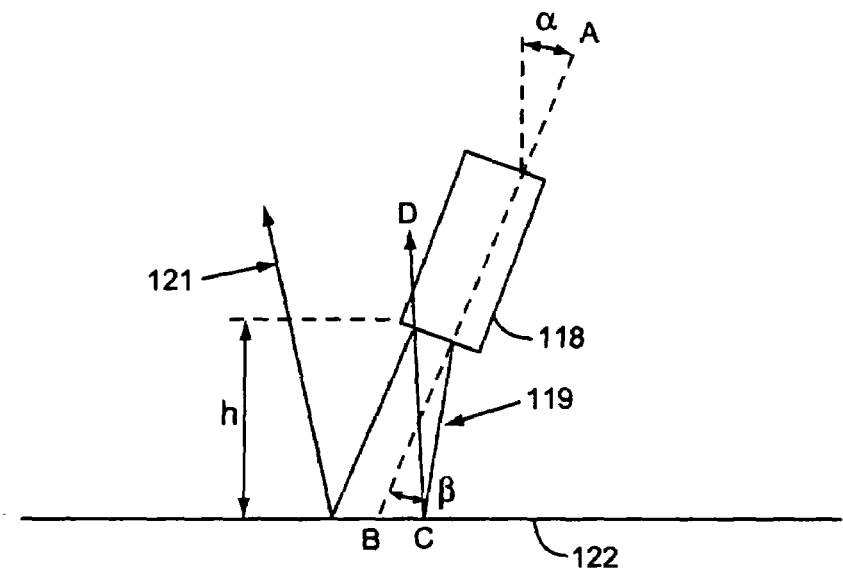
FIG. 3 is schematic diagram depicting the relationship between a collimator and a reflected light beam.

In the schematic diagram of FIG. 3, line AB is parallel to the collimator 118. α is the angle of the collimator 118 to a line normal to the surface of the target surface 122. β is the divergence of the incident light beam 119 coming from the collimator 118. The angle of incidence of the rightmost edge of the light beam 119 to the target surface 122 is α–β. That is, the rightmost edge of the beam 119 strikes the target surface 122 at an angle from a normal to the target surface 122 equal to α–β. If the beam 119 is specularly reflected, the rightmost edge of the beam 119 is reflected at the angle of incidence represented by line CD. It is important to keep light-absorbing objects out of the path of the specularly reflected beam 121.

There are two ways to accomplish this. The first is to simply keep the collimator 118 out of the path of the reflected beam 121. The second is to make sure that if the collimator 118 intrudes on the path of the reflected beam 121 that the surfaces of the collimator 118 that the light 121 strikes are as reflective as the interior walls 114 of the cavity 112. In this way there is no undue absorption of specularly reflected light 121 relative to diffusely reflected light.

Preferably, the angle α of the collimator 118 is in the range from about 5 degrees to about 30 degrees. More preferably, the angle α of the collimator 118 is about 15 degrees. In a representative embodiment of the present invention, the angle of divergence β of the incident light beam 119 is about 10 degrees. Therefore the angle of incidence of the right edge of the beam 119 is α–β or about 5 degrees. As the right hand edge of the reflected beam 121 returns toward the collimator 118 it will be to the left-hand side of the position where it emerges from the collimator 118, as shown by line CD (left and right are used herein only as reference directions with reference to FIG. 3; in practice the sensor 100 may assume any orientation). When the right edge of the reflected beam 121 nears the tip of the collimator 118, it will have moved left by a distance of about 2*h*tan (α–β), where h is the distance of the tip of the collimator 118 from the target surface 122. So either the left-hand edge of the collimator 118 must be to the right of this location, or any surfaces of the collimator 118 to the left of this position should be of the same material as the cavity walls.

In one embodiment, the distance h is about 8 mm. This means that any portion of the collimator 118 farther than 1.4 mm to the left of where the right edge of the beam 119 emerges from the collimator 118 must be highly and diffusely reflective. However, the collimator 118 works best if the interior is non-reflective or black and the exterior is white. In one embodiment, depicted in detail in FIG. 4, a shroud 123 is built into the structure of the cavity 112 to cover at least the left side of the collimator 118. Preferably, the shroud 123 surrounds the entire collimator 118. The shroud 123 is preferably made from the same material as the integrating cavity 112, and has surfaces that are diffusely highly reflective, as are all interior surfaces 114 of the cavity 112.

Figure 4:
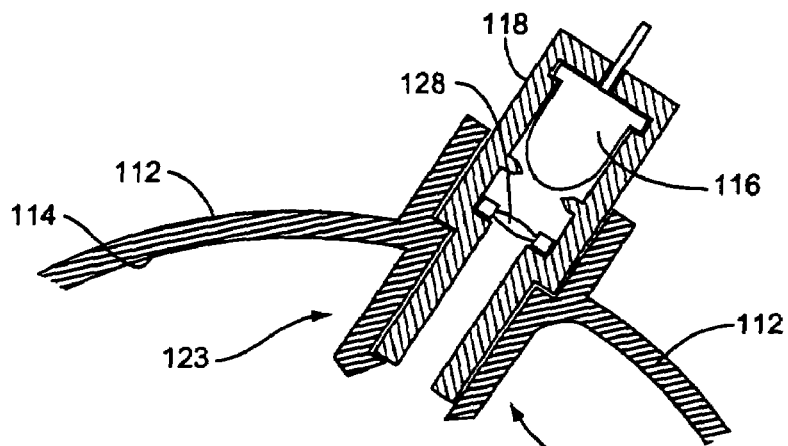
FIG. 4 is a partial section diagram depicting the position of a collimator in a shroud within an integrating cavity.

The optical source 116 is preferably an LED, as shown in FIG. 4. As known in the art, LEDs are compact, efficient, solid state light sources with high durability and reliability and long shelf and operational lifespans. LEDs require relatively little drive current, their intensity is easily controlled by varying the drive current, and LEDs generate little heat. The optical source 116 is more preferably an infrared LED, i.e., an LED that emits light in the infrared range of the electromagnetic spectrum. This is because all of the color toners in common use are reasonably reflective at infrared wavelengths. The lens 128 depicted in FIG. 4 is optional, as discussed below.

The optical sensor 124 is preferably a photodiode. As known in the art, a photodiode is a semiconductor diode in which the reverse current varies with illumination. Photodiodes are characterized by linearity of output over several magnitudes of light intensity, very fast response time, and a wide range of color response. Alternatively, the optical sensor 124 may be a phototransistor, a photojunction device in which current flow is proportional to the amount of incident light. The phototransistor is preferably operated in its linear region.

Figure 5:
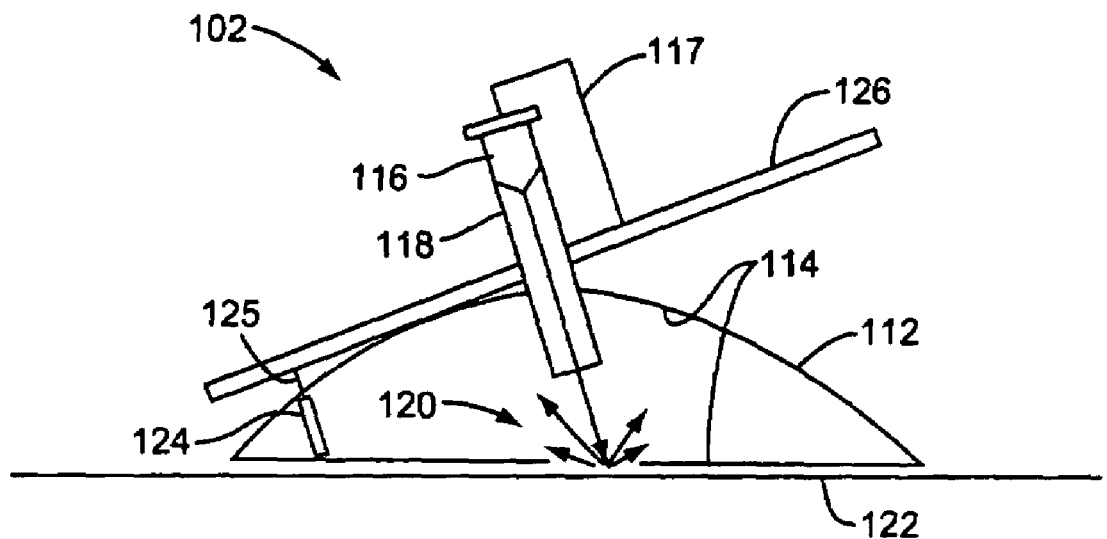
FIG. 5 is schematic diagram of an optical density sensor having a circuit card disposed proximate an optical detector.

Another embodiment of the optical density sensor according to the present invention is depicted in FIG. 5, wherein the various components have the same component numbering and functionality as previously described, and is indicated generally by the numeral 102. The optical density sensor 102 includes an integral circuit card 126, on which may be mounted, for example, an optical source drive circuit (not shown) and/or an optical detector sensing circuit (not shown). The close proximity of the circuit card 126 to the optical detector 124 moves the signal amplifier of an optical detector sensing circuit (not shown) closer to the signal source, further reducing the likelihood of picking up noise, and reducing the need for shielding of connectors 125. Similarly, the proximity of an optical source drive circuit (not shown) to the optical source 116 may increase operational efficiencies.

While the optical density sensor 102 is depicted in FIG. 5 with the collimator 118 extending into the integrating cavity 112 (as in the case of the sensor 100 depicted in FIG. 2), this is not necessary. The advantages of locating circuit components physically proximate the optical detector 124 accrue, even as applied to an optical density sensor having a collimator 118 positioned externally to the cavity 112, as known in the prior art. Naturally, the maximum benefit accrues from the combination of the two inventive concepts, as depicted in FIG. 5.

Figure 6:
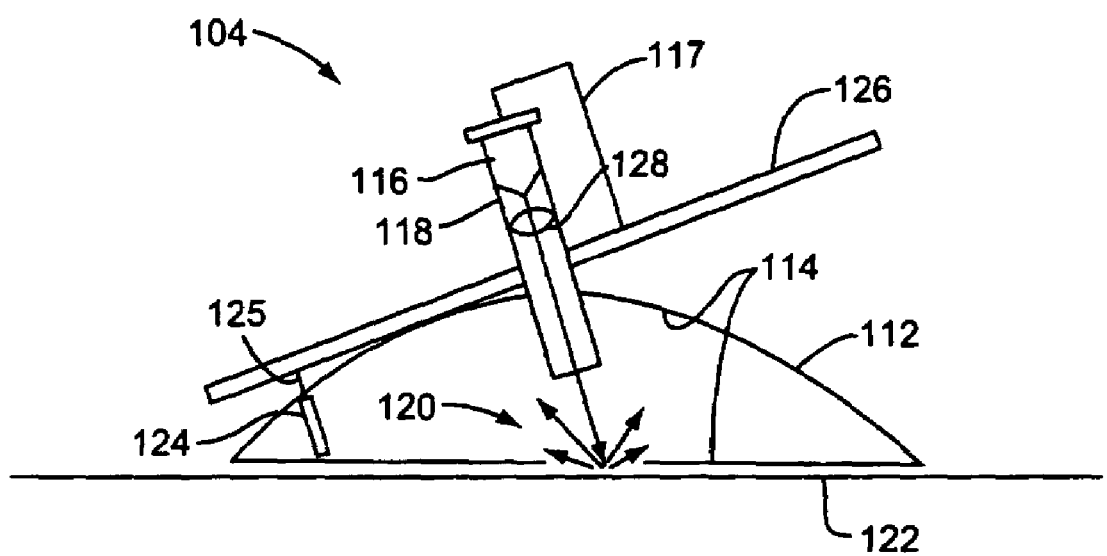
FIG. 6 is schematic diagram of an optical density sensor having a lens disposed in a collimator.

Yet another embodiment of the optical density sensor according to the present invention is depicted in FIG. 6, and indicated generally by the numeral 104. In this embodiment, a lens 128 is added to the collimator 118. A lens 128 positioned close to the optical source 116, as depicted in FIGS. 4 and 6, can focus light, which would otherwise be absorbed by the walls of the collimator 118, into a central portion of the beam, improving the brightness of the beam and the overall signal-to-noise ratio. Again, this benefit accrues independently of the positioning of the collimator 118 or the circuit card 126; however, all three inventive concepts are preferably employed together.

The standard practice for prior art integrating cavity reflectometers is to place the view port 120 in direct contact with the target surface 122 so that no light escapes. If a gap develops between the cavity 112 and the target surface 122, diffusely reflected light escapes the system and the signal intensity decreases. The loss in signal strength is directly proportional to the size of the gap between the cavity 112 and the target surface 122. Due to the nature of the application—to measure toner reflections as a belt or media sheet moves beneath the sensor 100, 102, 104, the cavity 112 cannot contact the target surface 122. There will inevitably be differences in the gap between the two in individual sensor 100, 102, 104 installations, and in many applications, the gap will vary with time.

Figure 7:
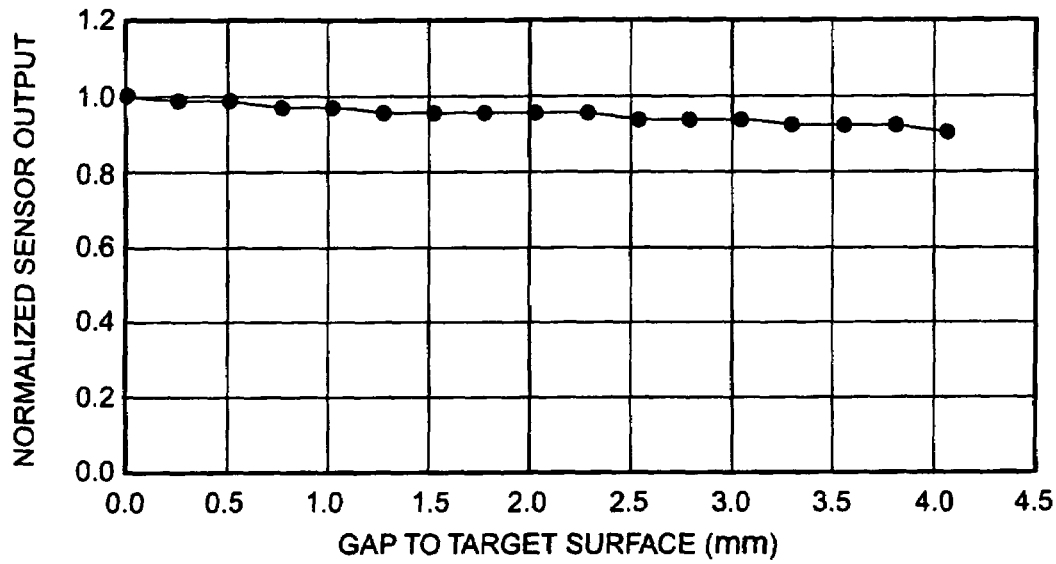
FIG. 7 is graph depicting optical detector signal strength as a function of gap size for a mostly specular reflecting target surface.
Figure 8:
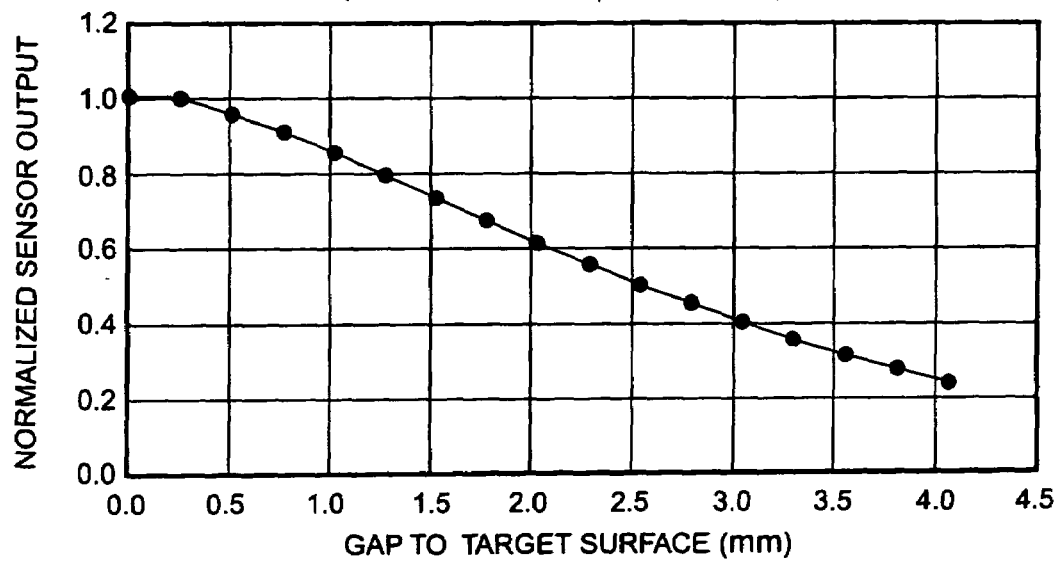
FIG. 8 is graph depicting optical detector signal strength as a function of gap size for a mostly diffuse reflecting target surface.

FIG. 7 shows the response of a prior art optical density sensor over a range of gaps to a largely specularly reflecting surface (a clean polycarbonate belt). The response is reasonably flat with respect to the gap because most of a specularly reflected optical beam will reflect back into the integrating cavity 112 through the viewing port 120 over a small range of gaps. A diffusely reflecting target, however, produces a dramatically different response. FIG. 8 depicts the response of the prior art optical density sensor over a range of gaps to a largely diffuse reflecting target (a yellow toner patch). The signal strength drops off rapidly with small increases in the gap size. The output signal is normalized to the value at zero gap.

At least two problems arise from this signal strength to gap size response. First, as discussed above, the variation in gap size over time precludes repeatable results. For example, the gap may vary +/−1 mm due to temperature variations, varying belt thickness, and the like. Second, measurements of the reflections of a surface that becomes more or less shiny over time, such as a belt, will vary even though the total reflection does not change.

Figure 9:
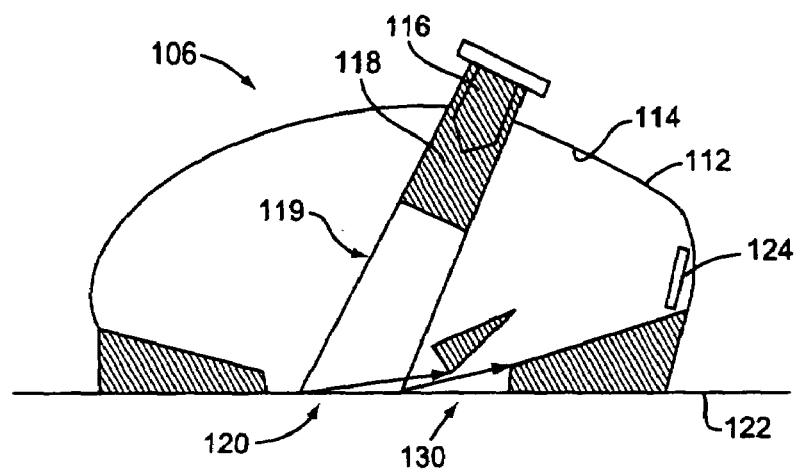
FIG. 9 is schematic diagram of an optical density sensor having a compensating slot, with zero gap from the target surface.

FIG. 9 depicts an optical density sensor according to the present invention, indicated generally by the numeral 106, that compensates for variations in the gap by deliberately allowing light reflected from the target surface 122 to illuminate the optical detector 124. This is something that would normally be avoided in an integrating cavity reflectometer of this type. Typically, only light reflected from the interior cavity walls 114 would be allowed to reach the optical detector 124. It is the diffuse reflection of the cavity interior walls 114 that combines the specular and diffuse components of the reflected light, creating an integrated signal. According to the present invention, allowing some of the diffusely reflected light to directly strike the optical detector 124 compensates for the diffusely reflected light lost through the gap between the cavity 112 and the target surface 122.

Figure 10:
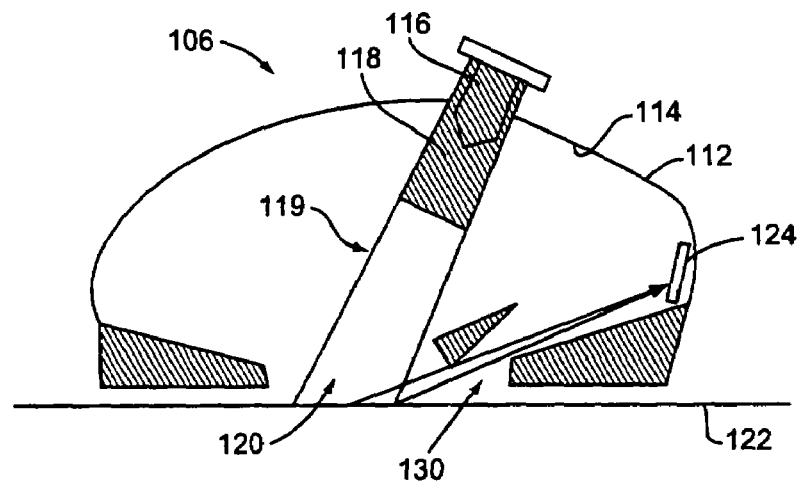
FIG. 10 is schematic diagram of an optical density sensor having a compensating slot, with slight gap from the target surface
Figure 11:
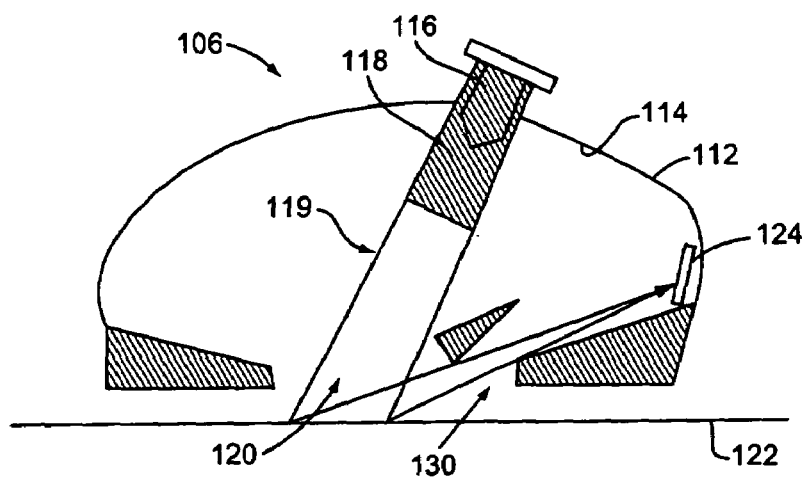
FIG. 11 is schematic diagram of an optical density sensor having a compensating slot, with large gap from the target surface.

A key parameter that must be controlled is the amount of the diffusely reflected light allowed to directly illuminate the optical detector 124 as the gap changes. According to the present invention, this is accomplished through the geometry of the parts. As depicted in FIGS. 9–11, a compensation slot 130 is formed in the base of the integrating cavity 112, in addition to the view port 120. Preferably, the position and configuration of the compensation slot 130 precludes any reflected light from the target surface 122 from reaching the optical detector 124 with zero gap between the cavity 112 and the target surface 122. As the gap increases, a correspondingly increasing amount of reflected light is allowed to directly impinge the optical detector 124. For the purpose of illustrating the operation of the compensation slot 130, the light exiting the collimator 118 is depicted as a beam 119.

FIG. 9 depicts the case of zero gap, i.e., the cavity 112 is in contact with the target surface 122. In this case, no light striking the target surface 122 is allowed to reflect directly back to the optical detector 124. In this case, the sensor 106 operates like a conventional, prior art reflectometer, with all of the light reflected from the target surface entering the integrating cavity 112 and striking interior walls 114 thereof, prior to reaching the optical detector 124.

FIG. 10 depicts the case of a small gap between the integrating cavity 112 and the target surface 122. In this case, some light diffusely reflected from the illuminated area of the target surface 122 is allowed to directly reach the optical detector 124 without first impinging on an interior cavity wall 114. However, the bulk of reflected light is still blocked from directly striking the optical detector 124.

As the gap between the cavity 112 and the target surface 122 increases, as depicted in FIG. 11, a larger portion of the illuminated area of the target surface 122 contributes light for the direct illumination of the optical detector 124. Thus, according to the present invention, the increase in gap size, which in prior art sensors would reduce the strength of an output signal of the optical detector 124, is compensated for by allowing a portion of the diffuse reflection to directly impinge the optical sensor 124.

Figure 12:
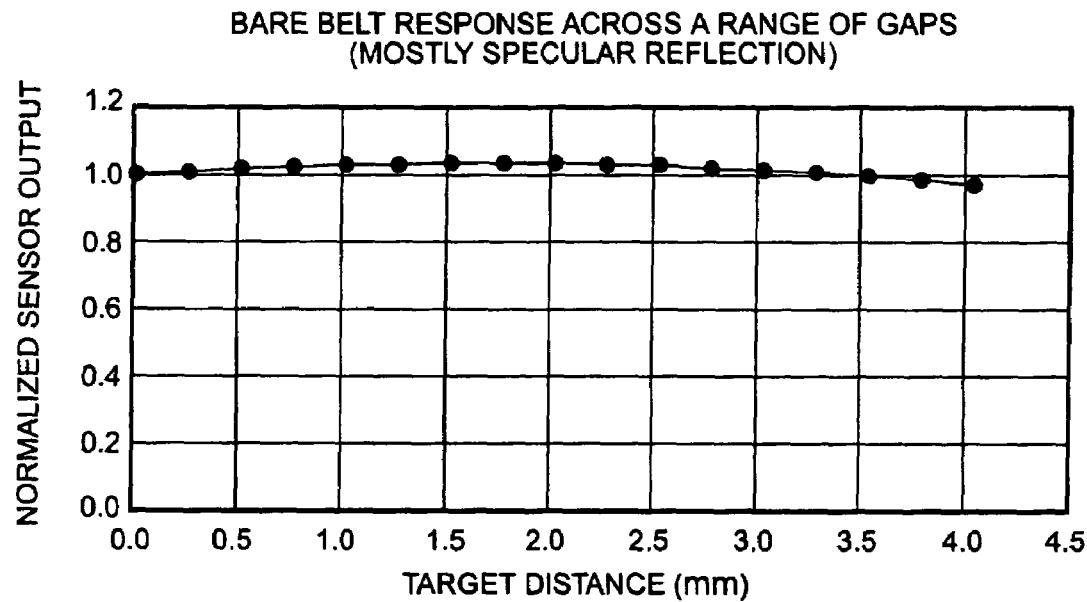
FIG. 12 is graph depicting optical detector signal strength as a function of gap size for a mostly specular reflecting target surface for an optical density sensor having a compensating slot.
Figure 13:
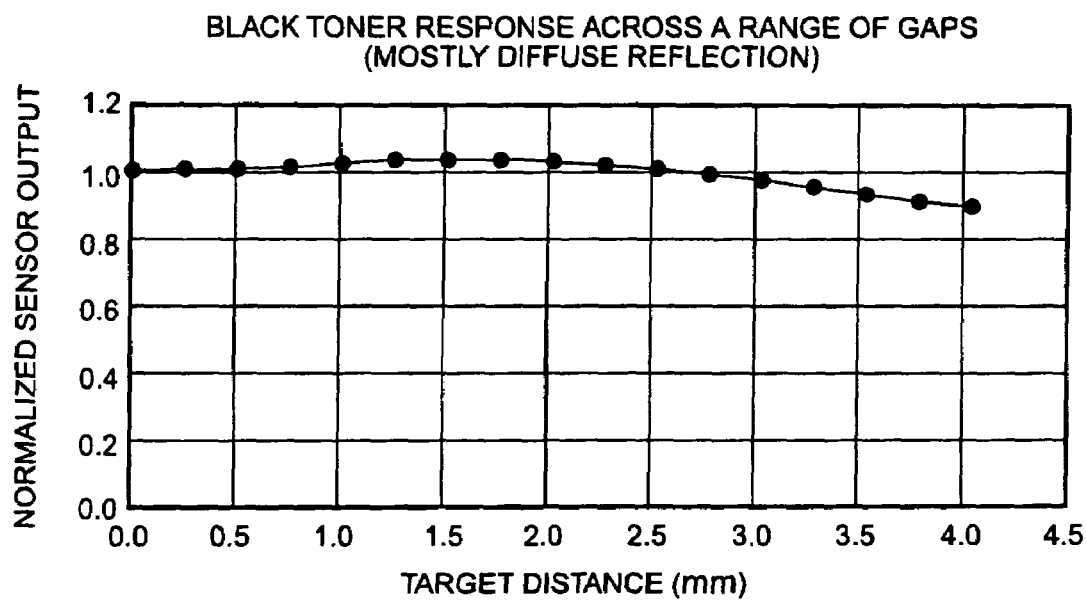
FIG. 13 is graph depicting optical detector signal strength as a function of gap size for a mostly diffuse reflecting target surface (black toner patch) for an optical density sensor having a compensating slot.
Figure 14:
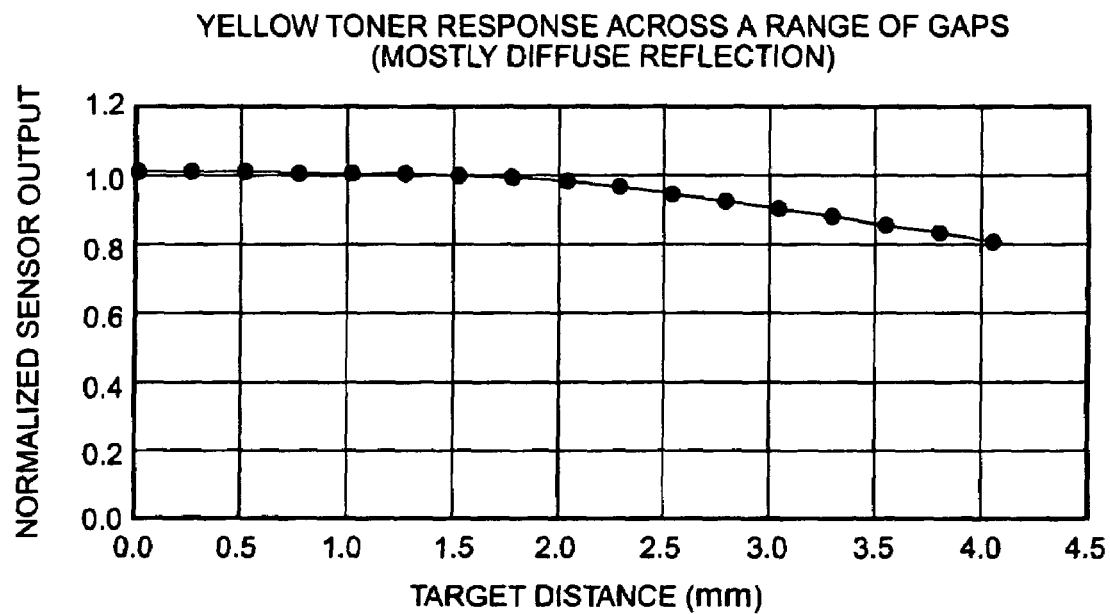
FIG. 14 is graph depicting optical detector signal strength as a function of gap size for a mostly diffuse reflecting target surface (yellow toner patch) for an optical density sensor having a compensating slot.
Figure 15:
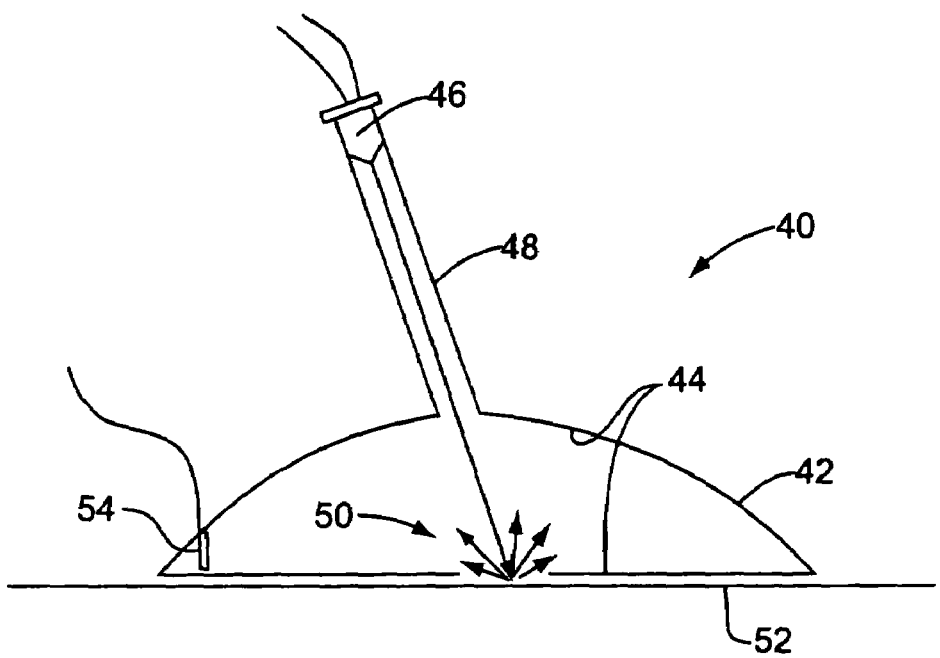
FIG. 15 is a schematic diagram of a prior art integrating cavity reflectometer type optical density sensor.

The efficacy of this approach is demonstrated by the graphs depicted in FIGS. 12–14. FIG. 12 depicts the response by gap size of a mostly specular target surface 122 (a clean belt). As expected (see FIG. 7), the response is largely flat with increasing gap size due to the largest component of the signal being specular reflection, which is directed into the integrating cavity 112, even with a significant gap.

The response of diffuse target surfaces 122 (such as toner), however, are striking (compare to FIG. 8). FIG. 13 depicts the response with a black toner patch as the target surface 122, and FIG. 14 depicts the response to a yellow toner patch. In both cases, the response is reasonably flat from a gap of zero to approximately three millimeters—a response similar to that obtained with mostly specular reflection (see FIG. 12). Thus, the optical density sensor 106 according to one embodiment of the present invention can tolerate a range of gaps between the cavity 112 and the target surface 122 while maintaining consistent output. The preferred gap size ranges from zero to about 3 mm.

While the optical density sensor 106 of FIGS. 9, 10 and 11 is depicted with the collimator 118 extending into the integrating cavity 112, this is not necessary to attain the gap-independence afforded by the compensating slot and direct illumination of the optical detector 124. Similarly, positioning a circuit card including an optical source drive circuit and/or an optical detector sensing circuit proximate the optical source 116 and optical detector 124, respectively, may impart additional advantages, but is not necessary to achieve the gap independence of the compensating slot 130. Further, providing a lens 128 within the collimator 118 may provide additional advantages as discussed above; however, this is not necessary to achieve the gap independence advantages of the compensation slot 130 of the present invention.

As used herein, the term "optical density" refers to the relative optical reflection from a surface. An optical density sensor is operative to sense and measure the total reflection—both specular and diffuse—from a target surface. In many applications, sensing the presence of toner is sufficient. For example, a registration process may require detecting the precise position of toner on a media sheet, which may be determined by detecting the presence of toner and timing that detection to the known position and/or speed of the sheet. In other applications, the degree, or density, of toner is calculated from the level of reflected light measured by the optical density sensor and calibration points stored in memory that relate the reflected light levels to toner density for various toner colors and formulations. As used herein, the term "sensing" toner refers to all such detection, measurement and calculation.

Although the present invention has been described herein with respect to particular features, aspects and embodiments thereof, it will be apparent that numerous variations, modifications, and other embodiments are possible within the broad scope of the present invention, and accordingly, all variations, modifications and embodiments are to be regarded as being within the scope of the invention. The present embodiments are therefore to be construed in all aspects as illustrative and not restrictive and all changes coming within the meaning and equivalency range of the appended claims are intended to be embraced therein.

What is claimed is:

1. An optical density sensor for sensing toner on a surface in an image forming device, comprising:
   an integrating cavity having a diffuse, reflective inner surface and having a view port formed therein;
   an optical source disposed in a collimator and positioned to illuminate said surface through said view port, said collimator extending into said integrating cavity; and
   an optical detector disposed within said integrating cavity outside of a direct optical path of said source.

2. The apparatus of claim 1 wherein said optical source is a light emitting diode.

3. The apparatus of claim 1 wherein said optical source emits infrared light.

4. The apparatus of claim 1 wherein said collimator is operative to focus light from said optical source through said view port and onto said surface, such that no light from said optical source directly strikes any interior surface of said integrating cavity.

5. The apparatus of claim 1 wherein said integrating cavity reflectometer further comprises a lens disposed in said collimator.

6. The apparatus of claim 1 wherein said optical detector is a photodiode.

7. The apparatus of claim 1 wherein said optical detector is a phototransistor.

8. The apparatus of claim 1 wherein said integrating cavity reflectometer further comprises a circuit card disposed proximate said optical source and detector.

9. The apparatus of claim 8 wherein said circuit card includes an optical detector sensing circuit.

10. The apparatus of claim 1 wherein said collimator is disposed within said integrating cavity at an angle from a direction normal to said surface in the range from about 5 degrees to about 30 degrees.

11. The apparatus of claim 10 wherein said collimator is disposed within said integrating cavity at an angle from a direction normal to said surface of about 15 degrees.

12. The apparatus of claim 1 wherein said integrating cavity includes a shroud covering at least part of said collimator, said shroud having a diffuse, reflective surface.

13. The apparatus of claim 1 wherein any portion of said collimator within said integrating cavity that is in the path of specular reflection from said surface, has a diffuse, reflective surface.

14. The apparatus of claim 1 wherein said integrating cavity further includes a compensating slot formed therein, said compensating slot operative to allow light reflected from said surface to directly strike said optical detector when said view port is spaced apart from said surface.

15. The apparatus of claim 1 wherein said surface is an intermediate transfer belt operative to transfer a developed toner image from one or more photoconductive members to a media sheet.

16. The apparatus of claim 1 wherein said surface is a media sheet.

17. The apparatus of claim 1 wherein said surface is a media sheet transport belt.

18. An optical density sensor for sensing toner on a surface in an image forming device, comprising:
   an integrating cavity having a diffuse, reflective inner surface and having a view port formed therein;
   an optical source positioned to illuminate said surface through said view port;
   an optical detector disposed within said integrating cavity outside of a direct optical path of said source; and
   a circuit card disposed proximate said optical source and optical detector, said circuit card including at least one of an optical source drive circuit and an optical detector sensing circuit.

19. The apparatus of claim 18 wherein said optical source is disposed in a collimator.

20. The apparatus of claim 19 wherein said collimator extends within the interior of said integrating cavity.

21. The apparatus of claim 19 wherein said collimator includes a lens.

22. The apparatus of claim 19 wherein said collimator is operative to focus light from said optical source through said view port and onto said surface, such that no light from said optical source directly strikes any interior surface of said integrating cavity.

23. The apparatus of claim 18 wherein said surface is an intermediate transfer belt operative to transfer a developed toner image from one or more photoconductive members to a media sheet.

24. The apparatus of claim 18 wherein said surface is a media sheet.

25. The apparatus of claim 18 wherein said surface is a media sheet transport belt.

26. An optical density sensor for sensing toner on a surface in an image forming device, comprising:
   an integrating cavity having a diffuse, reflective inner surface and having a view port formed therein;
   an optical source positioned to illuminate said surface through said view port;
   an optical detector disposed within said integrating cavity outside of a direct optical path of said source; and
   a compensating slot formed in said integrating cavity and positioned to allow light reflected from said surface to directly strike said optical detector when said view port is spaced apart from said surface.

27. The apparatus of claim 26 wherein said optical source is disposed in a collimator.

28. The apparatus of claim 27 wherein said collimator extends within the interior of said integrating cavity.

29. The apparatus of claim 27 wherein said collimator includes a lens.

30. The apparatus of claim 27 wherein said collimator is operative to focus light from said optical source through said view port and onto said surface, such that no light from said optical source directly strikes any interior surface of said integrating cavity.

31. The apparatus of claim 26 wherein said further comprising a circuit card disposed proximate said optical source and detector.

32. The apparatus of claim 31 wherein said circuit card includes an optical detector sensing circuit.

33. The apparatus of claim 26 wherein said surface is an intermediate transfer belt operative to transfer a developed toner image from one or more photoconductive members to a media sheet.

34. The apparatus of claim 26 wherein said surface is a media sheet.

35. The apparatus of claim 26 wherein said surface is a media sheet transport belt.

36. An optical density sensor for sensing toner on a surface in an image forming device, comprising:
   an integrating cavity having a diffuse, reflective inner surface and having a view port formed therein;
   an optical source disposed in a collimator and positioned to illuminate said surface through said view port, said collimator extending into said integrating cavity;
   an optical detector disposed within said integrating cavity outside of a direct optical path of said source;
   a circuit card disposed proximate said optical source and optical detector, said circuit card including at least one of an optical source drive circuit and an optical detector sensing circuit; and
   a compensating slot formed in said integrating cavity and positioned to allow light reflected from said surface to directly strike said optical detector when said view port is spaced apart from said surface.

37. The apparatus of claim 36 wherein said collimator includes a lens.

38. A method of sensing toner on a surface in an image forming device, comprising:
   illuminating said surface with an optical source;
   capturing light reflected from said source by said surface in an integrating cavity having diffuse, reflective inner surface, said reflected light passing through a view port formed in said cavity;
   sensing light reflected from the inner surface of said cavity onto an optical detector disposed within said cavity outside of a direct optical path of said source; and
   as said cavity moves apart from said surface, sensing light reflected from said source by said surface that directly strikes said optical detector, said light passing through a compensating slot formed in said cavity independent of said view port.

39. The method of claim 38 wherein the amount of light reflected by said surface directly striking said optical detector is directly proportional to the distance of said cavity from said slot.

40. The method of claim 38 wherein said light reflected from said source by said surface that directly strikes said detector compensates for the attenuation in light reflected from the inner surface of said cavity onto said optical detector due to the distance of said cavity from said surface.

* * * * *